United States Patent [19]

Minekane et al.

[11] Patent Number: 4,549,809
[45] Date of Patent: Oct. 29, 1985

[54] METHOD FOR PHOTOMETRIC MEASUREMENT OF LIGHT ABSORPTION OF LIQUID SAMPLES IN CUVETTES

[75] Inventors: Tomiharu Minekane; Noboru Yokotani, both of Otawara; Takehiko Onuma, Kurobane, all of Japan

[73] Assignee: Tokyo Shibaura Denki Kabushiki Kaisha, Japan

[21] Appl. No.: 536,790

[22] Filed: Sep. 28, 1983

[30] Foreign Application Priority Data

Sep. 30, 1982 [JP] Japan ................................ 57-171893

[51] Int. Cl.⁴ ............................................. G01N 21/00
[52] U.S. Cl. ..................................... 356/436; 356/409; 356/414; 422/64; 422/65
[58] Field of Search .................... 422/64, 65; 356/436, 356/409, 414

[56] References Cited

U.S. PATENT DOCUMENTS 3,966,323  6/1976  Matsuoka et al. .................... 356/96

Primary Examiner—Bernard D. Pianalto
Attorney, Agent, or Firm—Finnegan, Henderson, Farabow, Garrett & Dunner

[57] ABSTRACT

A photometric measurement method for producing readout signals indicative of light absorption of samples contained in a series of cylindrical cuvettes arranged in a movable cuvette carrier for successively conveying said cuvettes into the path of a measuring light beam directed onto a radiation detector, wherein readings are taken at precisely measured intervals as a function of the width of the cuvette, the rate of movement of the cuvette and the required number of measurements, and a selected reading is taken at the same distance from the leading wall of each cuvette.

5 Claims, 5 Drawing Figures

METHOD FOR PHOTOMETRIC MEASUREMENT OF LIGHT ABSORPTION OF LIQUID SAMPLES IN CUVETTES

BACKGROUND OF THE INVENTION

The present invention relates to a method for transmission type photometric measurement of liquid samples for the purpose of determining the concentration thereof and in particular to a method for the transmission type photometric measurement of liquid samples contained in a series of cells arranged in a cell carrier and successively conveyed by the latter into the path of a light beam which is directed onto a radiation detector, and for use in a spectrophotometers and an automatic analysis apparatus.

Transmission type photometric measurements are normally made by simply directing a light through a cell cuvette containing a fluid sample to be analyzed. A portion of the light beam is absorbed by the sample and the remaining portion passes through the cuvette to photodetector means for measurement. By comparing the measurement obtained from the sample with a measurement obtained from a control fluid the concentration of the analyzed sample can be calculated.

The total absorbance of the sample is known to be composed of the sum of the absorbances of the sample and a thermostaticized bath or the like.

A major source of error in the transmission type photometric apparatus lies in imperfections in the glass or plastic cuvette. Very minor variations in a cuvette will substantially affect measurements made by the photodetector means. The variety of the light passageways through the cuvette is one of the above-mentioned variations.

In order to compensate for the above-mentioned problem, highly accurate photometric measurement method utilizes optically ground and polished glass or quartz to form the square-shaped cuvettes having at least two sides which are parallel surfaces of extremely high uniformity. However, such cuvettes are very expensive to manufacture, and have the possibility of contamination between test samples due to improper cleaning. For this reason accuracy is normally sacrificed by using conventional cylindrical cuvettes resembling test tubes in transmission type photometric apparatus. There are changes in passageways of light through the cylindrical cuvette as the light beam laterally traverses the cross-sectional plane of the cuvette. When photometric apparatus is employed which passes light directly through the cylindrical cuvettes to a photodetector, substantial variation in light transmission results as the positions of photometric measurement are changed laterally in the cross-sectional plane of the moving cuvette.

SUMMARY OF THE INVENTION

An object of the present invention is to provide an improved transmission type photometric measurement method using cylindrical cuvettes.

Another object of the present invention is to provide a photometric measuring process which minimizes the effects of changes in the passageway of the measuring light beam through the cylindrical cuvette.

Briefly stated, in accordance with the present invention, the method for photometric measurement of the light absorption of a liquid sample in a cuvette comprises making the measurement of the light absorptions at precisely the same distance from the leading wall of each cuvette. This method is particularly advantageous when utilized in a process wherein a series of cuvettes or similar cells are moved successively at a uniform speed, or uniformly accelerated speed, through a light beam.

BRIEF DESCRIPTION OF THE DRAWINGS

The method by which the foregoing objects and features of the invention are achieved is pointed out with particularity in the claims forming the concluding portion of the specification. The method of the invention may be further understood by reference to the following description taken in connection with the following drawings in which:

DESCRIPTION OF THE PREFERRED EMBODIMENT

Figure 1:
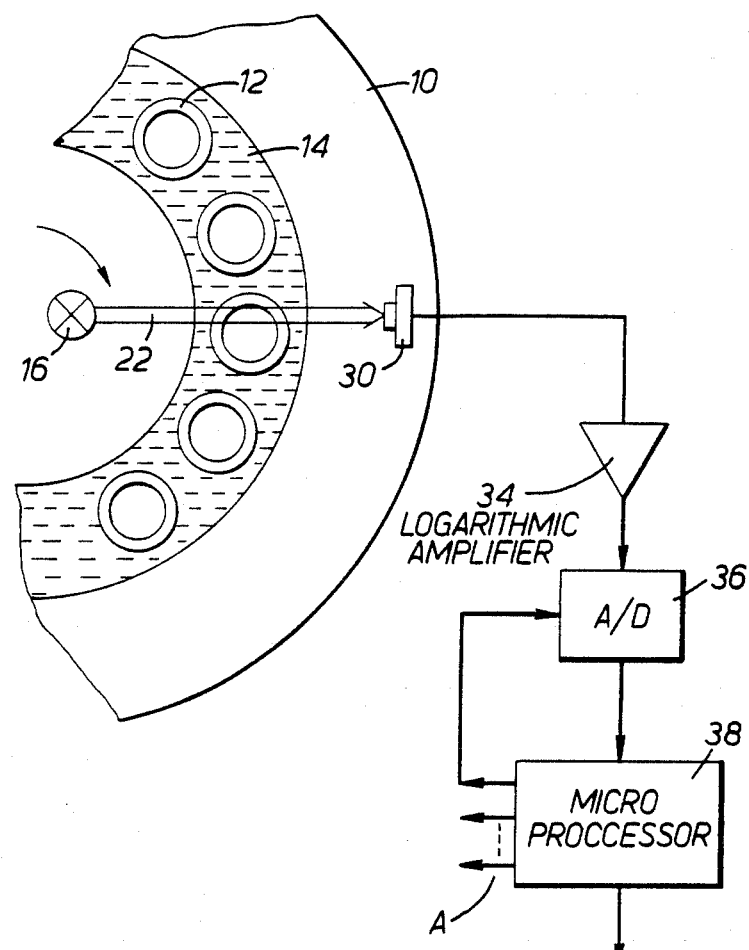
FIG. 1 is a schematic arrangement of apparatus for carrying out the method of the invention during the measurement of the light absorption of a sample.

FIG. 1 is an illustration of a photometric apparatus for carrying out the present invention wherein a cell carrier comprises a turntable 10 having a plurality of openings therein, into each of which a cylindrical cuvette 12 may be inserted. The cuvettes 12, as known, run in an annular thermostaticized liquid bath 14.

The cuvettes 12 contain one or more specific chemical reagents mixed in solution with a specific amount of the sample being tested.

Figure 2:
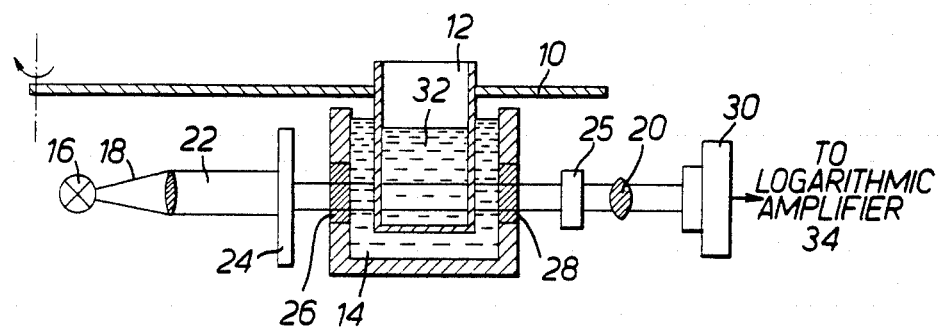
FIG. 2 is a vertical section through a portion of the apparatus of FIG. 1.

Upon insertion of a cuvette 12 in an opening in the turntable 10, the testing procedure begins a specific time thereafter. The radiant energy at a specific wavelength absorbed by each cuvette 12 and its contents is detected and an electrical signal having a magnitude proportional to that radiant energy absorption is applied to electric circuits within the analyzer. As may best be seen from FIG. 2 and is conventional, a light path existing from a radiant energy source 16, which is positioned within the turntable 10, is formed into a beam by lenses 18 and 20. This beam 22 passes through an iris 24 before passing through windows 26 and 28 of the bath 14. Radiant energy from the source 16 is directed through the reacted contents in a cuvette 12 to provide a resulting amount of light at a particular wavelength to a detector 30. The detector 30 may be made sensitive to the particular wavelength by an appropriate filter.

Upon rotation of the turntable 10, the different cuvettes 12 are successively moved through the path of the light beam 22. In intermediate positions the light beam 22 passes between the cuvettes 12, so as to pass only through the bath 14. The output of the detector 30 is supplied to the input of a logarithmic amplifier 34 for forming the logarithm of the signal. The analog outputs are all supplied to a multiplexer (not shown) which supplies analog outputs one at a time to an analog-to-digital converter 36 (A/D).

The absorbed amount of light at the above-mentioned wavelength is a Beer's law function of the optical density of the reacted contents in the cuvette 12. The outputs of the A/D 36 are optical density signals each indicative of an optical density value at the measuring positions across the cuvette 12.

Outputs are provided to a microprocessor 38 which includes a central processing unit (CPU), appropriate input/output (I/O) logic and a memory. The memory may include a read-only memory (ROM) and a random access memory (RAM).

The ROM memory will contain a series of computer instructions to be applied to control the CPU to provide signals through the I/O logic in a known manner. The RAM memory will be utilized for storing the outputs from the A/D 36. The output signals A (FIG. 1) from the microprocessor 38 are transmitted to the various sub-assemblies and portions within the apparatus, each of which enables a single sub-assembly or portion thereof within the apparatus to respond to the computer instructions. The microprocessor 38 provides periodic pulses to enable the A/D 36 to sample and hold instantaneous values coupled thereto from the amplifier 34. The A/D 36 may provide serial output.

Figure 3:
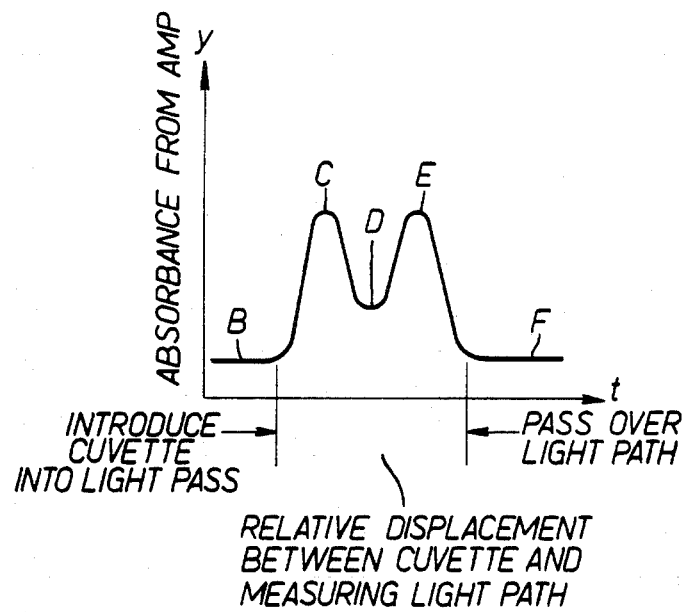
FIG. 3 is a graph illustrating the change in the absorption of light through a cylindrical cuvette containing a liquid sample as the cuvette is moved laterally across a light beam.

FIG. 3 illustrates changes in the absorption of light through a cuvette containing a liquid sample as the cuvette is laterally moved through the length of the diameter of the cuvette. These changes are caused by relative displacement between the cuvette 12 and the measuring light path 22. Portions B and F in FIG. 3 show the absorption when the light 22 passes only through the bath, portions C and E show the light absorption as the light beam 22 passes through the cuvette walls, and portion D shows the absorption as the light beam 22 passes only through the reacted contents in the cuvette 12.

In the method of the invention, measurements are taken of the light absorption of the cuvette and its contents at precisely timed intervals as the cuvette passes through the light beam at a predetermined rate of motion. A determination is made that the leading wall of the cuvette has passed through the light beam by comparing the differences between subsequent readings and an initial reading through the bath only until the difference exceeds a preselected limit G, less than the peak value of the readings of the leading wall. Since the diameter of the cuvette, the rate of movement of the cuvette, and the desired number of readings is known, the time intervals between readings can be calculated and the position of each reading, with respect to the cuvette, precisely determined.

It has been found that by using the measurement of light absorption at the same point along the path of movement as to each cuvette, the errors due to variations in the light absorption of the glass, or the materials, in the walls of the cuvette are unexpectedly reduced.

Figure 4:
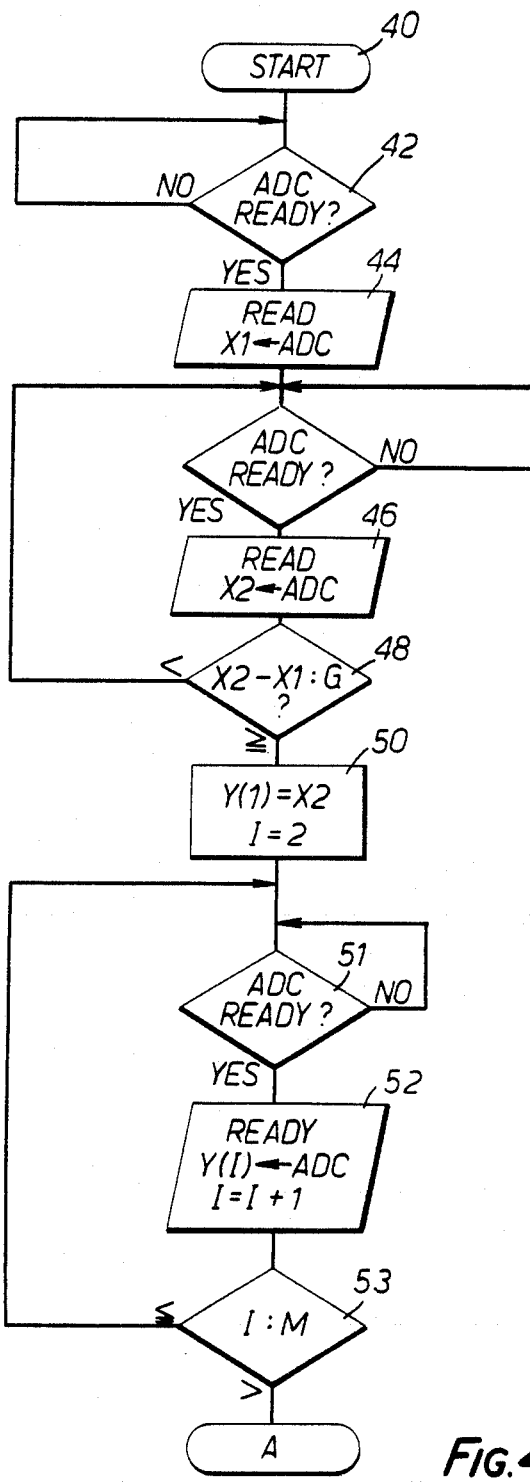
FIGS. 4 and 5 taken together are a flow chart illustrating the generation of output values based on readings taken in a manner according to the present invention.

Referring now to FIG. 4, a flow diagram of the computer program controlling microprocessor 38 immediately after the application of power will be described. At block 40 the processor 38 provides a code indicative of the photometric measurement being performed. At block 42, it is determined whether the A/D 36 is ready. If so, at blocks 44 and 46, a mean value X of a plurality of the absorption values taken is provided from A/D 36. The difference $(X_2-X_1)$ between the initial reading and the following reading, respectively, called $X_1$ and $X_2$, is provided, these readings being for the access B, as shown in FIG. 3, and the next reading.

At block 48, it is determined whether this difference $(X_2-X_1)$ exceeds a preselected limit G, less than the peak value corresponding to portion C, shown in FIG. 3, for example 10 m absorption. The radiant energy absorption is measured at specific times determined by the signals provided from a clock circuit (not shown), which provides clock signals to sub-assemblies and portions within the apparatus. A/D 36 converts the analog signal applied thereto to a two-byte digital signal in response to the enabling signal having the time interval T given by the following equation (1).

$$T = L/(V \times N) \quad (1)$$

Where L = the diameter of the cylindrical cuvette, V = the speed of movement of the cuvette, N = the number of samplings of optical density ($N \geq 30$).

After the conversion is completed, analog-to-digital converter (A/D) 36 provides READY status signal. In response to the READY status signal, the two-byte digital signal is transferred to microprocessor 38 via I/O logic from the A/D 36.

If the difference $(X_2-X_1)$ exceeds the preselected limit G at block 48, at block 50 the reading at that point is provided for storing in the memory for an ordering operation. For example, if the difference does not exceed the preselected limit G it is determined at block 51 whether A/D 36 is ready, and if so, at block 52 a further reading subsequent to the reading $X_2$ at block 50 is provided for storing in the memory in time. Both blocks 51 and 52 repeat until the number of the transferred readings is greater than a predetermined constant M.

The constant M is given by the following equation (2).

$$M = (S \times L)/(V \times T) \quad (2)$$

Where S = the safety coefficient which is equal to 1.2, L = the diameter of the cylindrical cuvette, V = the rate of movement of the cuvettes, and T is given by eq. (1).

Figure 5:
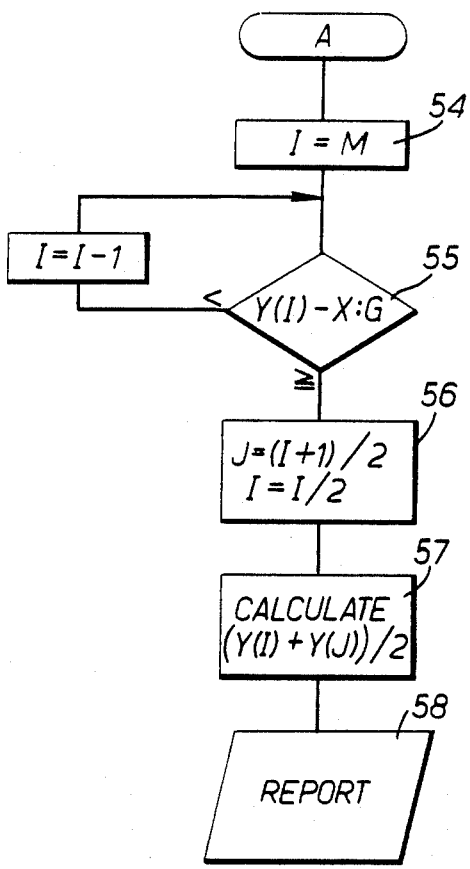

At block 53, it is determined whether the number I of the readings transferred to the memory of microprocessor 38 is greater than M. Block 53 leads to junction point A which is also marked in FIG. 5 to indicate the continuation of operation. Operation proceeds to block 54 at which the end reading of acquisition values is accessed from the memory in response to the constant M. The difference between the initial reading $X_1$ and the value Y(M) accessed from the memory, is provided. The difference between other values Y(I−1) may be taken. Block 54 proceeds to block 55 at which it is determined whether this difference exceeds the preselected value G. I is the subscript of the Y value.

If so, at block 56 data indicative of the trailing wall of the cylindrical cuvette is utilized to calculate the subscripts I and J indicative of the central portion of the cuvette. At block 57, the light absorptions and from that the optical density value corresponding to a specific position, such as the central portion of the cuvette, is calculated from data Y(I) and Y(J) whose subscripts are I, and J, respectively. An output is provided at block 58.

Since the measurements are taken at specific times, as measured by the clock circuit, it is a simple matter for anyone skilled in the art to have the computer select any one of the measurements through the central portions of the cuvette for use in the measurement of the absorption of the light by the reacted sample and thereby the density of the sample.

From the foregoing, it will be seen that this invention is well adapted to attain all of the ends and objects hereinbefore set forth, together with other advantages which are obvious and inherent. The improved photometric measurement method of the present invention cuvettes 12. As indicated, the variations in the cuvettes 12 do not substantially affect light transmission in the improved photometric measurement method herein described. It has been found that reproducible results are obtained under the method of the invention using inexpensive conventional cylindrical cuvettes.

Spectral analysis may be done if a diffraction grating replaces the interference filter as described above.

According to the present invention, optical density values of samples contained in the cuvette can be obtained based on distances from either walls of the cuvette.

Obviously, many modifications and variations of the invention, as hereinbefore set forth, can be made without departing from the spirit and scope thereof and therefore only such limitation should be imposed as are indicated by the appended claims.

What is claimed is:

1. A method of photometric measurement of the light absorption of the contents of a cuvette moving at a predetermined rate through the path of a beam of light directed onto a light detector comprising the steps of:
   a. fixing the time intervals between readings of the measurements of the light absorption as a function of the width of the cuvette, the predetermined rate of movement of the cuvette through the light path, and the required number of readings;
   b. making an initial reading of the light absorptions in the light path immediately before the cuvette enters the light path;
   c. comparing the differences between successive readings and the initial reading until the difference exceeds a predetermined limit less than the peak value of the readings of the leading wall of the cuvette, indicating passage of the leading wall and the arrival of a predetermined portion of the cuvette;
   d. continuing readings until the desired number of readings is taken indicating the passage of the trailing wall of the cuvette; and
   e. selecting a measurement of light absorption at exactly the same attained position as to each cuvette, as the predetermined portion of the cuvette passes through the path of the light beam.

2. The method of claim 1 including storing said width of the cuvette, predetermined rate of movement of the cuvette, the required number of readings, the predetermined limit in the memory of a microprocessor and making the required calculations in the microprocessor.

3. The method of claim 1 including a plurality of cuvettes arranged in a movable cuvette carrier, the cuvettes moving through a thermostaticized bath, or a like bath, and wherein said initial reading is taken through said bath.

4. The method of claim 1 including the step of converting the values output from said detector into digital form at predetermined times throughout the period of measurement of light absorption by the cuvette.

5. The method of claim 1 wherein said predetermined portion of the cuvette is the central portion thereof.

* * * * *